US005869084A

United States Patent [19]
Paradissis et al.

[11] Patent Number: 5,869,084
[45] Date of Patent: Feb. 9, 1999

[54] MULTI-VITAMIN AND MINERAL SUPPLEMENTS FOR WOMEN

[75] Inventors: George N. Paradissis, St. Louis; R. Saul Levinson; Gary Heeter, both of Chesterfield, all of Mo.; Robert C. Cuca, Edwardsville, Ill.; Patrick Paul Vanek, Ballwin, Mo.

[73] Assignee: K-V Pharmaceuticals Co., St. Louis, Mo.

[21] Appl. No.: 474,071

[22] Filed: Jun. 7, 1995

Related U.S. Application Data

[63] Continuation-in-part of Ser. No. 262,515, Jun. 20, 1994, abandoned.

[51] Int. Cl.$^6$ ................................................ A61K 47/00
[52] U.S. Cl. .......................... 424/439; 424/440; 426/73; 544/327; 514/905
[58] Field of Search ................... 424/440, 439; 426/73; 568/824; 544/327, 251; 552/653; 549/408; 514/905

[56] References Cited

U.S. PATENT DOCUMENTS

| | | |
|---|---|---|
| 2,218,591 | 10/1940 | Taylor . |
| 2,218,592 | 10/1940 | Taylor . |
| 4,431,634 | 2/1984 | Ellenbogen .............................. 424/648 |
| 4,629,625 | 12/1986 | Gaull ....................................... 424/643 |
| 4,670,247 | 6/1987 | Scialpi .................................... 424/484 |
| 4,710,387 | 12/1987 | Uiterwaal et al. ....................... 426/72 |
| 4,752,479 | 6/1988 | Briggs et al. ............................ 424/472 |
| 4,931,441 | 6/1990 | Lawrence ................................ 514/249 |
| 4,945,083 | 7/1990 | Jansen, Jr. ............................... 424/639 |
| 4,994,283 | 2/1991 | Mehansho et al. ..................... 424/439 |

FOREIGN PATENT DOCUMENTS

94/06415 of 1984 WIPO .

OTHER PUBLICATIONS

A.T. Diplock, "Antioxidant Nutrients and Disease Prevention: An Overview," 1895–1935, *Am. J. Clin. Nutr.*, 53, (1991).

*Documenta Ceigy, 7th Ed.,* (Diem, K. and Cemtuer, eds.), 457–497, Diba–Geigy Ltd., Ardsley, NY, (1975).

*Maternal Nutrition and the Course of Pregnancy, Summary Report,* 23, Appendix C, Committee on Maternal Nutrition/Food and Nutrition Board, National Research Council, National Academy of Sciences, U.S. Govt. Printing Office, Washington, D.C. (1970).

Whitehead, R.G., "Pregnancy and Lactation," in *Modern Nutrition in Health and Disease, 7th Ed.,* (Shils, M.E. and Young, V.R. eds.), 934, Lea & Febigers, Philadelphia (1988).

Rosso, P., ed., "Maternal Metabolism of Vitamins and Minerals," in *Nutrition and Metabolism in Pregnancy: Mother and Fetus,* 81–101, 118–132, Oxford Press (1990).

Hallberg, L., "Iron Balance in Pregnancy," in *Vitamins and Minerals in Pregnancy and Lactation,* (Berger, H., ed.), 115–127, Raven Press, New York (1988).

Glorieux, F. H. et al., "Calcium and Vitamin D, Status During Pregnancy," in *Vitamins and Minerals Pregnancy and Lactation,* 135–143, (Berger, H., ed.) Raven Press, New York (1988).

Worthington–Roberts, V. et al., "Physiological Basis of Nutritional Needs" in *Nutrition in Pregnancy and Lactation, 3rd Ed.,* 73–78, 120–131, Time Mirror/Mosby College Publishing (1985).

Chanarin, I., "Folate," in *Vitamins and Minerals in Pregnancy and Lactation,* (Berger, H., ed.), 129–134, Raven Press, New York (1988).

Schorah, C., "Importance of Adequate Folae Nutrition in Embryonic and Early Fetal Development," in *Vitamins and Minerals in Pregnancy and Lactation,* (Berger, H., ed.), 167–176, Raven Press, New York (1988).

Facsimile transmission from Mr. Suzanne Gaby to Gary Heeter, (Jan. 20, 1992) (information relating to vitamin and iron absorption).

Highest 1989 RDA, Current U.S. RDA and Proposed RDI for Vitamins and Minerals, (chart prepared from Part III, FDA Proposed Rules for Food Labeling Reference Daily Intakes, Fed. Red. 29476–29533, Jul. 19, 1990.

Physician's Desk Reference, 46th Edition, pp. 847–848, 972, 1214–1215, 1391, 1974–1975, 2250, 2273, Med Econ, Published (1992).

*Primary Examiner*—Thurman K. Page
*Assistant Examiner*—D. Faulkner
*Attorney, Agent, or Firm*—Gary M. Nath; Nath & Associates

[57] ABSTRACT

Multi-vitamin and mineral supplements for administration to lactating, non-lactating, and menopausal women, which comprise specific regimens of critical nutritional agents. The supplements are specifically tailored to meet nutritional requirements and maintain a woman's health during each stage of life.

51 Claims, No Drawings

MULTI-VITAMIN AND MINERAL SUPPLEMENTS FOR WOMEN

RELATED APPLICATION

This application is a Continuation-in-Part application of U.S. patent application Ser. No. 08/262,515 filed Jun. 20, 1994 now abandoned, the entire contents of which are incorporated herein in their entirety.

BACKGROUND OF THE INVENTION

1. Field of the Invention

The present invention relates to multi-vitamin and mineral supplements, and particularly to multi-vitamin and mineral supplements for administration to women during different stages of life.

2. Description of Related Art

Vitamin and mineral preparations are commonly administered to treat specific medical conditions or as general nutritional supplements. Recent studies have elucidated the important physiological roles played by vitamins and minerals, and established a correlation between deficiencies or excesses of these nutrients and the etiologies of certain disease states in humans. See, e.g., Diplock, "Antioxidant Nutrients and Disease Prevention: An Overview," Am. J. Clin. Nutr., 53:189–193 (1991); Document Geigy Scientific Tables, 457–497 (Diem and Cemtuer eds., 7th ed., 1975).

It has further become recognized that various life-stage groups of the human population require different quantities and types of vitamins and minerals to prevent or alleviate diseases, as well as to maintain general good health. For example, it is known that pregnant women commonly require iron therapy to prevent or treat iron-deficiency anemia. Various prior patents have been directed to improving the efficacy of iron supplements for use during pregnancy.

U.S. Pat. No. 4,994,283, for example, discloses nutritional mineral supplements which include iron and calcium compounds in combination with citrates or tartrates, ascorbates, and fructose. The tendency of calcium to inhibit the bioavailability of iron is said to be reduced in such compositions, so that the conjoint bioavailability of these two minerals is enhanced.

U.S. Pat. No. 4,431,634 maximizes the bioavailability of iron in prenatal iron supplements by maintaining the amount of calcium compounds in the supplement at 300 mg or less and the amount of magnesium compounds at 75 mg or less per dosage unit.

Another approach to the same problem is found in U.S. Pat. No. 4,752,479, wherein a multi-vitamin and mineral dietary supplement is provided which includes (a) one or more divalent dietary mineral components such as calcium or magnesium; and (b) a bioavailable iron component, presenting a controlled release form and adapted to be released in a controlled manner in the gastrointestinal tract.

U.S. Pat. No. 4,710,387 discloses a nutritional supplement preparation for pregnant and breast-feeding women which contains 10–20% by weight of protein, 16–28% by weight of fat, 43–65% by weight carbohydrates, and at most 3.5% by weight of moisture, minerals, trace elements and vitamins.

Despite the foregoing efforts to improve vitamin and mineral supplementation for pregnant women, conventional prenatal supplements are not ideally suited for women during other phases of their lives. For example, the nutritional needs of lactating women following a pregnancy differ from the needs during pregnancy. The vitamin/mineral requirements for non-lactating and menopausal women also differ from the requirements of pregnant women.

Conventional nutritional formulations are poorly designed for administration to women during various stages of life in which the physiological requirements of the women vary significantly. It would therefore be desirable to provide a multi-vitamin and mineral supplement which obviates this deficiency of known vitamin/mineral products.

SUMMARY OF THE INVENTION

The present invention overcomes the shortcomings of known nutritional supplements by providing multi-vitamin and mineral supplements which are specifically tailored for administration to lactating, non-lactating, and menopausal women. The formulations of the invention have been found to maximize the benefits of vitamin and mineral supplementation for women by specifically formulating the products to meet the physiological requirements of women during these life stages.

The compositions of the invention include certain essential nutritional components in dosage levels which have been found to optimize the maintenance of the women's health during each of the noted stages of life. Minerals such as calcium, zinc and iron are dosed (i.e. provided in the supplement) in the form of a corresponding pharmaceutically acceptable compound.

According to a first aspect of the invention, a multi-vitamin and mineral supplement for administration to a lactating woman is provided. This supplement is specially designed to aid in fulfilling the dietary needs of women who are producing and secreting milk, that is, lactating women. The supplement comprises:

(a) from about 350 mg to about 480 mg of elemental calcium dosed in the form of a pharmaceutically acceptable calcium compound;
(b) from about 400 I.U. to about 600 I.U. of Vitamin D;
(c) from about 400 I.U. to about 1200 I.U. of Beta carotene, or about 3600 I.U. to about 10,000 I.U. of Vitamin A or mixtures thereof;
(d) from about 9.6 mcg to about 14.4 mcg of Vitamin $B_{12}$;
(e) from about 8 mg to about 12 mg of Vitamin $B_6$;
(f) from about 20 mg to about 30 mg of Vitamin $B_3$;
(g) from about 2.7 mg to about 4.0 mg of Vitamin $B_2$;
(h) from about 3.2 mg to about 4.6 mg of Vitamin $B_1$;
(i) from about 24 I.U. to about 36 I.U. of Vitamin E;
(j) from about 28 mg to about 43 mg of elemental iron, dosed in the form of a pharmaceutically acceptable iron compound; and
(k) from about 20 mg to about 30 mg of elemental zinc, dosed in the form of a pharmaceutically acceptable zinc compound.

A multi-vitamin and mineral supplement for administration to a non-lactating woman is also provided by the invention. This supplement is designed to aid in fulfilling the dietary needs of women during the period after puberty and before menopause who are neither pregnant nor lactating. This formulation comprises:

(a) from about 160 mg to about 240 mg of elemental calcium dosed in the form of a pharmaceutically acceptable calcium compound;
(b) from about 320 I.U. to about 480 I.U. of Vitamin D;
(c) from about 250 I.U. to about 750 I.U. of Beta-carotene or from about 3,600 I.U. to about 5,400 I.U. of Vitamin A or mixtures thereof;
(d) from about 9.6 mcg to about 14.4 mcg of Vitamin $B_{12}$;

(e) from about 8 mg to about 12 mg of Vitamin $B_6$;
(f) from about 20 to about 30 mg of Vitamin $B_3$;
(g) from about 2.7 mg to about 4 mg of Vitamin $B_2$;
(h) from about 3.2 mg to about 4.8 mg of Vitamin $B_1$;
(i) from about 24 I.U. to about 36 I.U. of Vitamin E;
(j) from about 39 mg to about 42 mg of elemental iron dosed in the form of a pharmaceutically acceptable iron compound; and
(k) from about 20 mg to about 30 mg of elemental zinc dosed in the form of a pharmaceutically acceptable zinc compound.

A multi-vitamin and mineral supplement for administration to a menopausal woman is also provided. This supplement is specially designed to aid in fulfilling the dietary needs of women during the transitional period marked by the cessation of menses. Menopausal women may be asymptomatic or experience a variety of symptoms including hot flushes. See The Merck Manual of Diagnosis and Therapy 15th edition, 1713–1715. Most menopausal women experience hot flushes for over a year and 25 to 50% experience hot flushes for more than five years. The supplement for menopausal women of the present invention comprises:

(a) from about 320 mg to about 480 mg of elemental calcium dosed in the form of a pharmaceutically acceptable calcium compound;
(b) from about 320 I.U. to about 480 I.U. of Vitamin D;
(c) from about 250 I.U. to about 750 I.U. of Beta-carotene, or form about 3,600 I.U. to 5,400 I.U. of Vitamin A and mixtures thereof;
(d) from about 20 mcg to about 30 mcg of Vitamin $B_{12}$;
(e) from about 2.4 mg to about 3.6 mg of Vitamin $B_6$;
(f) from about 16 mg to about 24 mg of Vitamin $B_3$;
(g) from about 1.3 mg to about 2.0 mg of Vitamin $B_2$;
(h) from about 1.2 mg to about 1.8 mg of Vitamin $B_1$;
(i) from about 70 I.U. to about 110 I.U. of Vitamin E;
(j) from about 7 mg to about 11 mg of elemental iron dosed in the form of a pharmaceutically acceptable iron compound;
(k) from about 16 mg to about 24 mg of elemental zinc dosed in the form of a pharmaceutically acceptable zinc compound;
(l) from about 40 mcg to about 60 mcg of elemental molybdenum dosed in the form of a pharmaceutically acceptable molybdenum compound;
(m) from about 80 mcg to about 120 mcg of elemental chromium dosed in the form of a pharmaceutically acceptable chromium compound.

Thus, the invention provides the above-described multi-vitamin and mineral supplements for administration to lactating, non-lactating, and menopausal women. In contrast to conventional vitamin and mineral products, the formulations of the invention comprise specific regimens of critical nutritional agents, in order to better meet the physiological requirements of women and maintain good health throughout life.

DESCRIPTION OF THE PREFERRED EMBODIMENTS

The invention provides multi-vitamin and mineral supplements which are specifically tailored for administration to lactating, non-lactating, and menopausal women. The formulations of the invention include certain essential nutritional components in dosage levels which have been found to optimize the maintenance of a women's health during each of these stages of life.

According to a first aspect of the invention, a multi-vitamin and mineral supplement for administration to a lactating woman is provided, which comprises:

(a) from about 320 mg to about 480 mg of elemental calcium dosed in the form of a pharmaceutically acceptable calcium compound;
(b) from about 400 I.U. to about 600 I.U. of Vitamin D;
(c) from about 400 I.U. to about 1200 I.U. of Beta-carotene, or about 3600 I.U. to about 10,000 I.U. of Vitamin A or mixtures thereof;
(d) from about 9.6 mcg to about 14.4 mcg of Vitamin $B_{12}$;
(e) from about 8 mg to about 12 mg of Vitamin $B_6$;
(f) from about 20 mg to about 30 mg of Vitamin $B_3$;
(g) from about 2.7 mg to about 4 mg of Vitamin $B_2$;
(h) from 3.2 mg to about 4.8 mg of Vitamin $B_1$;
(i) from about 24 I.U. to about 36 I.U. of Vitamin E;
(j) from about 28 mg to about 43 mg of elemental iron dosed in the form of a pharmaceutically acceptable iron compound; and
(k) from about 20 mg to about 30 mg of elemental zinc dosed in the form of a pharmaceutically acceptable zinc compound.

A particularly preferred multi-vitamin and mineral supplement for lactating women also includes from about 160 mg to about 240 mg of a pharmaceutically acceptable magnesium compound and about 95 mg to about 145 mg of Vitamin C.

A multi-vitamin and mineral supplement for administration to a non-lactating woman is also provided by the invention. The formulation comprises:

(a) from about 160 mg to about 240 mg of elemental calcium dosed in the form of a pharmaceutically acceptable calcium compound;
(b) from about 320 I.U. to about 480 I.U. of Vitamin D;
(c) from about 250 I.U. to about 750 I.U. of Beta-carotene or from about 3,600 I.U. to about 5,400 I.U. of Vitamin A or mixtures thereof;
(d) from about 9.6 mcg to about 14.4 mcg of Vitamin $B_{12}$;
(e) from about 8 mg to about 12 mg of Vitamin $B_6$;
(f) from about 20 mg to about 30 mg of a Vitamin $B_3$;
(g) from about 2.7 mg to about 4 mg of Vitamin $B_2$;
(h) from about 3.2 mg to about 4.8 mg of Vitamin $B_1$;
(i) from about 24 I.U. to about 36 I.U. of Vitamin E;
(j) from about 39 mg to about 42 mg of elemental iron dosed in the form of a pharmaceutically acceptable iron compound; and
(k) from about 20 mg to, about 30 mg of elemental zinc dosed in the form of a pharmaceutically acceptable zinc in the zinc compound.

A particularly preferred multi-vitamin and mineral supplement for lactating women also includes from about 160 mg to about 240 mg of a pharmaceutically acceptable magnesium compound and about 95 mg to about 145 mg of Vitamin C.

A multi-vitamin and mineral supplement for administration to a menopausal women is also provided, which comprises:

(a) from about 320 mg to about 480 mg of elemental calcium dosed in the form of a pharmaceutically acceptable calcium compound;
(b) from about 320 I.U. to about 480 I.U. of Vitamin D;

(c) from about 250 I.U. to about 750 I.U. of Beta-carotene or from about 3,600 I.U. to about 5,400 I.U. of Vitamin A and mixtures thereof;

(d) from about 20 mcg to about 30 mcg of Vitamin $B_{12}$;

(e) from about 2.4 mg to about 3.6 mg of Vitamin $B_6$;

(f) from about 16 mg to about 24 mg of Vitamin $B_3$;

(g) from about 1.3 mg to about 2.0 mg of Vitamin $B_2$;

(h) from about 1.2 mg to about 1.8 mg of Vitamin $B_1$;

(i) from about 70 I.U. to about 110 I.U. of Vitamin E;

(j) from about 7 mg to about 11 mg of elemental iron dosed in the form of a pharmaceutically acceptable iron compound;

(k) from about 16 mg to about 24 mg of elemental zinc dosed in the form of a pharmaceutically acceptable zinc compound;

(l) from about 40 mcg to about 60 mcg of element molybdenum dosed in the form of a pharmaceutically acceptable molybdenum compound; and (m) from about 80 mcg to about 120 mcg of elemental chromium dosed in the form of a pharmaceutically acceptable chromium compound.

A particularly preferred multi-vitamin and mineral supplement for menopausal women also includes bout 160 mg to about 240 mg of a pharmaceutically acceptable magnesium compound.

It will be noted that the formulations vary in the critical nutritional agents included and amounts thereof. For example, because calcium is essential for the production of milk, levels of calcium are higher for administration to lactating women than in the non-lactating and menopausal formulations. As menopausal women do not lose iron like women with menstrual cycles, the amount of iron in the menopausal formulation is reduced greatly in comparison to the formulations for lactating and non-lactating women. Molybdenum and chromium are added to the menopausal formulation because these agents are believed to assist the immune system, which is a useful therapy in older women.

Useful pharmaceutically acceptable calcium compounds include any of the well-known calcium supplements, such as calcium carbonate, calcium phosphate, calcium citrate, calcium sulfate, calcium oxide, calcium hydroxide, calcium apatite, calcium citrate-maleate, calcium lactate, calcium levulinate and the like. Preferably, calcium compounds selected from the group consisting of calcium carbonate, calcium sulfate, and mixtures thereof are employed.

Useful pharmaceutically acceptable zinc compounds include zinc sulfate, zinc chloride, and zinc oxide, with zinc sulfate being preferred.

The pharmaceutically acceptable iron compound may be chosen from any of the well-known iron II (ferrous) or iron III (ferric) supplements, such as ferrous fumarate, ferrous sulfate, carbonyl iron, ferrous glucomate, ferrous chloride, ferrous lactate, ferrous tartrate, ferrous succinate, ferrous glutamate, ferrous citrate, ferrous pyrophosphate, ferrous cholinisocitrate, ferrous carbonate, iron-sugar-carboxylate complexes and the like.

Preferably, the iron compound comprises a pharmaceutically acceptable iron compound coated with a pharmaceutically acceptable film forming material which permits release of the iron in the intestine of a woman administered the supplement. Suitable coatings include any material know in the art for forming enteric, controlled release, or sustained release coatings, such as cellulose ethers including hydroxypropyl methylcellulose, methylcellulose, ethylcellulose, and carboxymethylcellulose; cellulose esters such as cellulose acetate, cellulose acetate phthalate, and cellulose nitrate; acrylate and methacrylate copolymers; and the like. The coated iron compound has been found to provide increased iron bioavailability by minimizing interaction between the iron compound and divalent cations such as calcium in the nutritional supplement. Release of the iron in the intestine also minimizes stomach upset.

It is also possible in the present formulations to combine various forms of extended release particles or coatings along with immediate release particles or coatings to deliver the various vitamins and mineral supplements over various rates of release. For example, certain agents such as Thiamine, Niacinamide, Pyridoxine, Ascorbic Acid, Folic Acid, Iron and Riboflavin could be released over an extended period of time from two hours up to 24 hours while other agents such as Beta-carotene, Vitamin A, Vitamin $D_3$, Vitamin $B_{12}$, Biotin, Pantothenic Acid, Copper, Zinc, Magnesium, Potassium, Iodine, Chromium, Molybdenum and Selenium can be administered as immediate release. The ability to obtain extended and immediate release characteristics is performed using well known procedures and techniques available to the ordinary skilled artisan.

The multi-vitamin and mineral supplements of the invention may include additional nutritional components well-known in the art. For example, the supplements may include elemental magnesium dosed in the form of one or more pharmaceutically acceptable magnesium compounds, such as magnesium stearate, magnesium carbonate, magnesium oxide, magnesium hydroxide, and magnesium sulfate. Magnesium stearate is a preferred form of the compound. The formulations may also include Vitamin C, from about 0.1 mg to about 1 mg of folic acid, from 1 mg to about 3 mg of copper, and from about 0.05 mg to about 0.25 mg of iodine. Other nutritional agents well-known in the art may be included as desired.

In a preferred embodiment of the formulations, the optional Vitamin C and folic acid nutritional components are coated to provide controlled release of these agents. Techniques and materials discussed above that are utilized to coat iron are preferred.

Pharmaceutically acceptable copper compounds include cupric oxide, cupric sulfate, or cupric gluconate, with cupric oxide being preferred. Preferred pharmaceutically acceptable iodine compounds include sodium or potassium iodide, with potassium iodide being most preferred.

The nutritional supplements of the invention may be provided in any suitable dosage form known in the art. For example, the compositions may be incorporated into tablets, powders, granules, beads, chewable lozenges, capsules, liquids, or similar conventional dosage forms, using conventional equipment and techniques know in the art. Tablet dosage forms are preferred.

Furthermore, the dosage form can be in the form of a bi-layer tablet composed of at least one extended-release layer and at least one immediate-release layer. Also, the bi-layer tablet can be coated for ease of administration or can be enteric coated to reduce any gastric irritation and the unpleasant "burping" produced by the vitamins and minerals. Also, multi-particulate design of extended-release and immediate-release components can be enteric coated and compressed into a tablet or filled into hard or soft gelatin capsules.

When preparing dosage forms incorporating the compositions of the invention, the nutritional components are normally blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethyl cellulose and sodium starch glycolate; suspending agents, such as povidone, polyvinyl alcohol and the like; absorbent, such as silicon dioxide; preservatives, such as methylparaben, propylparaben, and sodium benzoate; surfactants, such as sodium lauryl sulfate, polysorbate 80, and the like; and colorants, such as F.D. & C dyes and lakes.

For preparing compositions from the compounds described by this invention, inert, pharmaceutically acceptable carriers can be used which are either solid or liquid. Solid form preparations include powders, tablets, dispersible granules, capsules, and cachets. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compounds. In the tablet the active compound is mixed with carrier having the necessary binding properties in suitable proportions and compacted in the shape and size desired. The powders and tablets preferably contain from 5 or 10 to about 90 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, coca butter, and the like. The term "preparation" is intended to include the formulation of the active compounds with encapsulating material as carrier providing a capsule in which the active component (with or without other carriers) is surrounded by carrier, which is thus in association with it. Similarly, cachets are included. Tablets, powders, cachets, and capsules can be used a solid dosage forms suitable for oral administration. Liquid form preparations include solutions, suspensions, and emulsions. As an example, water or water/ propylene glycol solutions for parenteral injection may be used. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigerations in order to retard possible decomposition.

The solid and liquid forms may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the preparations are in unit dosage form. In such form, the preparation is subdivided into unit doses containing appropriate quantities of the active components. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied according to the particular application and the potency of the active ingredients.

Determination of the proper dosage for a particular situation is within the skill of the art. For convenience, the total daily dosage may be divided and administered in portions during the day if desired or at one time, morning, afternoon, night as well as biphasic, triphasic, etc. Controlled and uncontrolled release formulations are also contemplated.

Although the products of the invention are preferably intended for administration to humans, it will be understood that the formulation may also be utilized in veterinary therapies for other animals.

The following examples are given to illustrate the invention but are not deemed to be limiting thereof. All amounts specified in the application are based on milligrams unless otherwise indicated. The term "I.U." represents International Units.

EXAMPLE 1

Preparation of Multi-Vitamin and Mineral Supplements

The following compositions were used to prepare multi-vitamin and mineral supplements for administration to lactating, non-lactating, and menopausal women:

TABLE I

| Component | Lactating | Non-Lactating | Menopausal |
| --- | --- | --- | --- |
| Calcium, mg | 320–480 | 160–240 | 320–480 |
| Vitamin D, I.U. | 400–600 | 320–480 | 320–480 |
| Beta-carotene, I.U. | 400–1200 | 250–750 | 250–750 |
| Vitamin $B_{12}$, mcg | 9.6–14.4 | 9.6–14.4 | 20–30 |
| Vitamin $B_6$, mg | 8–12 | 8–12 | 2.4–3.6 |
| Vitamin $B_3$, mg | 20–30 | 20–30 | 16–24 |
| Vitamin $B_2$, mg | 2.7–4.0 | 2.7–4.0 | 1.3–2.0 |
| Vitamin $B_1$, mg | 3.2–4.8 | 3.2–4.8 | 1.2–1.8 |
| Vitamin E, I.U. | 24–36 | 24–36 | 70–110 |
| Iron, mg | 28–43 | 39–42 | 7–11 |
| Zinc, mg | 20–30 | 20–30 | 16–24 |
| Vitamin C, mg | 95–145 | 95–175 | 190–300 |
| Molybdenum, mcg | 20–30 | 40–60 | 40–60 |
| Chromium, mcg | 40–60 | 80–120 | 80–120 |
| Vitamin A, I.U. | 3,600–10,000 | 3,600–5,400 | 3,600–5,400 |
| Potassium, mg. | 40–60 | 40–60 | 64–96 |
| Pantothenic Acid, mg | 12–18 | 8–12 | 8–12 |
| Folic Acid, mg | 0.8–1.2 | 0.4–0.8 | 0.4–0.6 |
| Biotin, mcg | 40–60 | 240–360 | 240–360 |
| Copper, mg | 1.6–2.4 | 1.6–2.4 | 1.6–2.4 |
| Iodine, mcg | 120–180 | 120–180 | 120–180 |
| Magnesium, mg | 160–240 | 160–240 | 160–240 |
| Selenium, mcg | 50–70 | 50–70 | 50–70 |
| Phosphorous, mg | 320–480 | 160–240 | 320–480 |

Tablets incorporating the above formulations were prepared using conventional methods and materials known in the pharmaceutical art. The resulting nutritional supplement tablets were recovered and stored for future use.

EXAMPLE 2

The following compositions were used to prepare a multi-vitamin and mineral supplement for administration to lactating, non-lactating and menopausal women.

TABLE II

| Component | Lactating | Non-Lactating | Menopausal |
|---|---|---|---|
| Calcium, mg | 400 | 200 | 400 |
| Vitamin D, I.U. | 500 | 400 | 400 |
| Beta-carotene, I.U. | 8000 | 5000 | 5000 |
| Vitamin $B_{12}$, mcg | 12 | 20 | 25 |
| Vitamin $B_6$, mg | 10 | 4 | 3 |
| Vitamin $B_3$, mg | 25 | 20 | 20 |
| Vitamin $B_2$, mg | 3.4 | 3.4 | 1.7 |
| Vitamin $B_1$, mg | 4 | 3 | 1.5 |
| Vitamin E, I.U. | 30 | 75 | 90 |
| Iron, mg | 36 | 18 | 9 |
| Zinc, mg | 25 | 15 | 20 |
| Vitamin C, mg | 120 | 200 | 240 |
| Molybdenum, mcg | 25 | 50 | 50 |
| Chromium, mcg | 50 | 100 | 100 |
| Potassium, mg | — | 50 | 80 |
| Pantothenic Acid, mg | 15 | 10 | 10 |
| Folic Acid, mg | 1 | 0.6 | 0.5 |
| Biotin, mcg | 50 | 300 | 300 |
| Copper, mg | 2 | 2 | 2 |
| Iodine, mcg | 150 | 150 | 150 |
| Magnesium, mg | 200 | 200 | 200 |

The invention being thus described, it will be apparent that the same may be varied in many ways. such variations are not to be regarded as a departure from the spirit and scope of the invention, and all such modifications are intended to be within the scope of the appended claims.

We claim:

1. A multi-vitamin and mineral supplement for administration to a lactating woman, which comprises:
    (a) from about 320 mg to about 480 mg of elemental calcium dosed in the form of a pharmaceutically acceptable calcium compound;
    (b) from about 400 I.U. to about 600 I.U. of Vitamin D;
    (c) from about 400 I.U. to about 1200 I.U. of Beta-carotene or about 3,600 I.U. to about 10,000 I.U. of Vitamin A or mixtures thereof;
    (d) from about 9.6 mcg to about 14.4 mcg of Vitamin $B_{12}$;
    (e) from about 8 mg to about 12 mg of Vitamin $B_6$;
    (f) from about 20 mg to about 30 mg of Vitamin $B_3$;
    (g) from about 2.7 mg to about 4 mg of Vitamin $B_2$;
    (h) from about 3.2 mg to about 4.8 mg of Vitamin $B_1$;
    (i) from about 24 I.U. to about 36 I.U. of Vitamin E;
    (j) from about 28 mg to about 43 mg of elemental iron dosed in the form of a pharmaceutically acceptable iron compound; and
    (k) from about 20 mg to about 30 mg of elemental zinc dosed in the form of a pharmaceutically acceptable zinc compound.

2. The multi-vitamin and mineral supplement of claim 1, wherein the pharmaceutically acceptable calcium compound is selected from the group consisting of calcium carbonate, calcium phosphate, calcium citrate, calcium sulfate, calcium oxide, calcium hydroxide, calcium apatite, calcium citrate-maleate, calcium lactate, calcium levulinate and the like.

3. The multi-vitamin and mineral supplement of claim 1, which further comprises from about 160 mg to about 240 mg of a pharmaceutically acceptable magnesium compound.

4. The multi-vitamin and mineral supplement of claim 3, wherein the pharmaceutically acceptable magnesium compound is selected from the group consisting of magnesium hydroxide, magnesium sulfate, magnesium oxide, magnesium stearate, magnesium carbonate.

5. The multi-vitamin and mineral supplement of claim 1, wherein the pharmaceutically acceptable iron compound comprises a pharmaceutically acceptable iron selected from ferrous fumarate, ferrous sulfate, carbonyl iron, ferrous glucomate, ferrous chloride, ferrous lactate, ferrous tartrate, ferrous succinate, ferrous glutamate, ferrous citrate, ferrous pyrophosphate, ferrous cholinisocitrate, ferrous carbonate, iron-sugar-carboxylate complexes and the like, coated with a pharmaceutically acceptable film forming material which permits release of the iron in the intestine of a woman administered the supplement.

6. The multi-vitamin and mineral supplement of claim 5, wherein the iron is in the form of an extended release iron to be released over a two to twenty-four hour period.

7. The multi-vitamin and mineral supplement of claim 1, wherein certain components are formulated to release over an extended period of time.

8. The multi-vitamin and mineral supplement of claim 1, wherein certain components are formulated as immediate release components.

9. The multi-vitamin and mineral supplement of claim 1, wherein certain agents such as Thiamine, Niacinamide, Pyridoxine, Ascorbic Acid, Folic Acid, Iron and Riboflavin are released over an extended period of time from six hours up to twenty-four hours while other agents such as Beta-carotene, Vitamin A, Vitamin $D_3$, Vitamin $B_{12}$ Biotin Pantothenic Acid, Copper, Zinc, Magnesium, Potassium Iodine, Chromium Molybdenum and Selenium are administered as immediate release agents.

10. The multi-vitamin and mineral supplement of claim 1, wherein the pharmaceutically acceptable zinc compound is selected from the group consisting of zinc oxide, zinc sulfate, and zinc chloride.

11. The multi-vitamin and mineral supplement of claim 1, further comprising from about 95 mg to about 145 mg of Vitamin C.

12. The multi-vitamin and mineral supplement of claim 1, further comprising a pharmaceutically acceptable carrier material.

13. The multi-vitamin and mineral supplement of claim 1, which is administered orally once per day.

14. The multi-vitamin and mineral supplement of claim 1, wherein the total daily dosage is divided and administered in portions during the day.

15. The multi-vitamin and mineral supplement of claim 1, wherein the dosage form is in the form of a bi-layer tablet composed of an extended-release layer and an immediate-release layer.

16. The multi-vitamin and mineral supplement of claim 15, wherein the bi-layered tablet is coated for ease of administration or enteric coated to reduce gastric irritation.

17. The multi-vitamin and mineral supplement of claim 1, wherein the dosage form is enteric coated and compressed into a tablet or filled into hard or soft gelatin capsules.

18. A multi-vitamin and mineral supplement for administration to a non-lactating woman, which comprises:
    (a) from about 160 mg to about 240 mg of elemental calcium dosed in the form of a pharmaceutically acceptable calcium compound;
    (b) from about 320 I.U. to about 480 I.U. of Vitamin D;
    (c) from about 250 I.U. to about 750 I.U. of Beta-carotene or from about 3,600 I.U. to about 5;400 I.U. of Vitamin A or mixtures thereof;

(d) from about 9.6 mcg to about 14.4 mcg of Vitamin $B_{12}$;
(e) from about 8 mg to about 12 mg of Vitamin $B_6$;
(f) from about 20 mg to about 30 mg of Vitamin $B_3$;
(g) from about 2.7 mg to about 4 mg of Vitamin $B_2$;
(h) from about 3.2 mg to about 4.8 mg of Vitamin $B_1$;
(i) from about 24 I.U. to about 36 I.U. of Vitamin E;
(j) from about 39 mg to about 42 mg of elemental iron dosed in the form of a pharmaceutically acceptable iron compound; and
(k) from about 20 mg to about 30 mg of elemental zinc dosed in the form of a pharmaceutically acceptable zinc compound.

19. The multi-vitamin and mineral supplement of claim 18, wherein the pharmaceutically acceptable calcium compound is selected from the group consisting of calcium carbonate, calcium phosphate, calcium citrate, calcium sulfate, calcium oxide, calcium hydroxide, calcium apatite, calcium citrate-maleate, calcium lactate, calcium levulinate and the like.

20. The multi-vitamin and mineral supplement of claim 18, which further comprises from about 160 mg to about 240 mg of a pharmaceutically acceptable magnesium compound.

21. The multi-vitamin and mineral supplement of claim 20, wherein the pharmaceutically acceptable magnesium compound is selected from the group consisting of magnesium hydroxide, magnesium sulfate, magnesium oxide, magnesium stearate, and magnesium carbonate.

22. The multi-vitamin and mineral supplement of claim 18, wherein the pharmaceutically acceptable iron compound comprises a pharmaceutically acceptable iron selected from ferrous fumarate, ferrous sulfate, carbonyl iron, ferrous glucomate, ferrous chloride, ferrous lactate, ferrous tartrate, ferrous succinate, ferrous glutamate, ferrous citrate, ferrous pyrophosphate, ferrous cholinisocitrate, ferrous carbonate, iron-sugar-carboxylate complexes and the like, coated with a pharmaceutically acceptable film forming material which permits release of the iron in the intestine of a woman administered the supplement.

23. The multi-vitamin and mineral supplement of claim 22, wherein the iron is in the form of an extended release iron to be released over a two to twenty-four hour period.

24. The multi-vitamin and mineral supplement of claim 18, wherein certain components are formulated to release over an extended period of time.

25. The multi-vitamin and mineral supplement of claim 18, wherein vitamins and minerals independently selected from the group consisting of Beta-carotene, Vitamin A, Vitamin $D_3$, Vitamin $B_{12}$, Biotin, Pantothenic Acid, Copper, Zinc, Magnesium, Potassium, Iodine, Chromium, Molybdenum and Selenium are formulated as immediate release components.

26. The multi-vitamin and mineral supplement of claim 18, wherein certain agents such as Thiamine, Niacinamide, Pyridoxine, Ascorbic Acid, Folic Acid, Iron and Riboflavin are released over an extended period of time from six hours up to twenty-four hours while other agents such as Beta-carotene, Vitamin A, Vitamin $D_3$, Vitamin $B_{12}$, Biotin Pantothenic Acid, Copper, Zinc, Magnesium, Potassium Iodine, Chromium Molybdenum and Selenium are administered as immediate release agents.

27. The multi-vitamin and mineral supplement of claim 18, wherein the pharmaceutically acceptable zinc compound is selected from the group consisting of Zinc Oxide, Zinc Sulfate, and Zinc Chloride.

28. The multi-vitamin and mineral supplement of claim 18, further comprising from about 95 mg to about 175 mg of Vitamin C.

29. The multi-vitamin and mineral supplement of claim 18, further comprising a pharmaceutically acceptable carrier material.

30. The multi-vitamin and mineral supplement of claim 18, which is administered orally once per day.

31. The multi-vitamin and mineral supplement of claim 18, wherein the total daily dosage is divided and administered in portions during the day.

32. The multi-vitamin and mineral supplement of claim 31, wherein the dosage form is in the form of a bi-layer tablet composed on an extended-release layer and an immediate-release layer.

33. The multi-vitamin and mineral supplement of claim 32, wherein the bi-layered tablet is coated for ease of administration or enteric to reduce gastric irritation.

34. The multi-vitamin and mineral supplement of claim 18, wherein the dosage form is enteric coated and compressed into a tablet or filled into hard or soft gelatin capsules.

35. A multi-vitamin and mineral supplement for administration to a menopausal woman, which comprises:
(a) from about 320 mg to about 480 mg of elemental calcium dosed in the form of a pharmaceutically acceptable calcium compound;
(b) from about 320 I.U. to about 480 I.U. of Vitamin D;
(c) from about 250 I.U. to about 750 I.U. of Beta-carotene or from about 3,600 I.U. to about 5,400 I.U. of Vitamin A and mixtures thereof;
(d) from about 20 mcg to about 30 mcg of Vitamin B12;
(e) from about 2.4 mg tQ about 3.6 mg of Vitamin $B_6$;
(f) from about 16 mg to about 24 mg of Vitamin B3;
(g) from about 1.3 mg to about 2.0 mg of Vitamin B2;
(h) from about 1.2 mg to about 1.8 mg of Vitamin $B_1$;
(i) from about 70 I.U. to about 110 I.U. of Vitamin E;
(j) from about 7 mg to about 11 mg of elemental iron dosed in the form of a pharmaceutically acceptable iron compound;
(k) from about 16 mg to about 24 mg of elemental zinc dosed in the form of a pharmaceutically acceptable zinc compound;
(l) from about 40 mcg to about 60 mcg of elemental molybdenum dosed in the form of a pharmaceutically acceptable molybdenum compound; and
(m) from about 80 mcg to about 120 mcg of elemental chromium dosed in the form of a pharmaceutically acceptable chromium compound.

36. The multi-vitamin and mineral supplement of claim 35, wherein the pharmaceutically acceptable calcium compound is selected from the group consisting of calcium carbonate, calcium phosphate, calcium citrate, calcium sulfate, calcium oxide, calcium hydroxide, calcium apatite, calcium citrate-maleate, calcium lactate, calcium levulinate and the like.

37. The multi-vitamin and mineral supplement of claim 35, which further comprises from about 160 mg to about 240 mg of a pharmaceutically acceptable magnesium compound.

38. The multi-vitamin and mineral supplement of claim 35, wherein the pharmaceutically acceptable magnesium compound is selected from the group consisting of magnesium hydroxide, magnesium sulfate, magnesium oxide, magnesium stearate, and magnesium carbonate.

39. The multi-vitamin and mineral supplement of claim 35, which is administered orally once per day.

40. The multi-vitamin and mineral supplement of claim 35, wherein the total daily dosage is divided and administered in portions during the day.

41. The multi-vitamin and mineral supplement of claim 35, wherein the iron is in the form of an extended release iron to be released over a six to twenty-four hour period.

42. The multi-vitamin and mineral supplement of claim 35, wherein certain components are formulated to release over an extended period of time.

43. The multi-vitamin and mineral supplement of claim 35, wherein certain components are formulated as immediate release components.

44. The multi-vitamin and mineral supplement of claim 35, wherein certain agents such as Thiamine, Niacinamide, Pyridoxine, Ascorbic Acid, Folic Acid, Iron and Riboflavin are released over an extended period of time from six hours up to twenty-four hours while other agents such as Beta-carotene, Vitamin A, Vitamin $D_3$, Biotin Pantothenic Acid, Copper, Zinc, Magnesium, Potassium Iodine, Chromium Molybdenum and Selenium are administered as immediate release agents.

45. The multi-vitamin and mineral supplement of claim 35, wherein the dosage form is in the form of a bi-layer tablet composed of an extended-release layer and an immediate-release layer.

46. The multi-vitamin and mineral supplement of claim 45, wherein the bi-layered tablet is coated for ease of administration or enteric to reduce gastric irritation.

47. The multi-vitamin and mineral supplement of claim 35, wherein the dosage form is enteric coated and compressed into a tablet or filled into hard or soft gelatin capsules.

48. A multi-vitamin and mineral supplement for administration to a lactating woman, which comprises:
   (a) from about 320 mg to about 480 mg of elemental calcium dosed in the form of a pharmaceutically acceptable calcium compound;
   (b) from about 400 I.U. to about 600 I.U. of Vitamin D;
   (c) from about 400 I.U. to about 1200 I.U. of Beta-carotene or about 3,600 I.U. to about 10,000 I.U. of Vitamin A;
   (d) from about 9.6 mcg to about 14.4 mcg of Vitamin $B_{12}$;
   (e) from about 20 mg to about 30 mg of Vitamin $B_3$;
   (f) from about 2.7 mg to about 4 mg of Vitamin $B_2$;
   (g) from about 3.2 mg to about 4.8 mg of Vitamin $B_1$;
   (h) from about 24 I.U. to about 36 I.U. of Vitamin E;
   (i) from about 20 mg to about 30 mg of elemental zinc dosed in the form of a pharmaceutically acceptable zinc compound.

49. The multi-vitamin and mineral supplement of claim 48, wherein the total daily dosage is divided and administered in portions throughout the day.

50. A multi-vitamin and mineral supplement for administration to a menopausal woman, which comprises:
   (a) from about 320 mg to about 480 mg of elemental calcium dosed in the form of a pharmaceutically acceptable calcium compound;
   (b) from about 320 I.U. to about 480 I.U. of Vitamin D;
   (c) from about 20 mcg to about 30 mcg of Vitamin $B_{12}$;
   (d) from about 16 mg to about 24 mg of Vitamin $B_3$;
   (e) from about 1.3 mg to about 2.0 mg of Vitamin $B_2$;
   (f) from about 1.2 mg to about 1.8 mg of Vitamin $B_2$;
   (g) from about 70 I.U. to about 110 I.U. of Vitamin E;
   (h) from about 7 mg to about 11 mg of elemental iron dosed in the form of a pharmaceutically acceptable iron compound;
   (i) from about 16 mg to about 24 mg of elemental zinc dosed in the form of a pharmaceutically acceptable zinc compound.

51. The vitamin and mineral supplement of claim 50, wherein the total daily dosage is divided and administered in portions throughout the day.

* * * * *

UNITED STATES PATENT AND TRADEMARK OFFICE
CERTIFICATE OF CORRECTION

Page 1 of 2

PATENT NO. : 5,869,084
DATED : Feb. 9, 1999
INVENTOR(S) : Paradissis et al.

It is certified that error appears in the above-identified patent and that said Letters Patent is hereby corrected as shown below:

Claim 26, line 57, 58 replace "Biotin Pantothenic"

with --Biotin, Pantothenic--

Claim 26, line 58, 59 replace "Potassium Iodine,"

with --Potassium, Iodine,--

Claim 26, line 59, replace "Chromium Molybdenum"

with --Chromium, Molybdenum--

Claim 35, line 30, replace "mg tQ" with --mg to--

Claim 44, line 16, replace "Potassium Iodine,"

with --Potassium, Iodine,--

Claim 44, line 16, 17, replace "Chromium Molybdenum"

with --Chromium, Molybdenum--

UNITED STATES PATENT AND TRADEMARK OFFICE
CERTIFICATE OF CORRECTION

PATENT NO. : 5,869,084
DATED : Feb. 9, 1999
INVENTOR(S) : Paradissis et al.

It is certified that error appears in the above-identified patent and that said Letters Patent is hereby corrected as shown below:

Claim 50, line 25, replace "1.8 mg of Vitamin $B_2$;"
    with --1.8 mg of Vitamin $B_1$;--

Signed and Sealed this

Thirteenth Day of July, 1999

Attest:

Q. TODD DICKINSON

*Attesting Officer*    *Acting Commissioner of Patents and Trademarks*